US006184924B1

(12) United States Patent
Schneider et al.

(10) Patent No.: US 6,184,924 B1
(45) Date of Patent: Feb. 6, 2001

(54) METHOD AND DEVICE FOR THE AUTOMATIC DETECTION OF SURFACE DEFECTS FOR CONTINUOUSLY CAST PRODUCTS WITH CONTINUOUS MECHANICAL REMOVAL OF THE MATERIAL

(75) Inventors: Volker Rainer Schneider; Hans-Joachim Braach, both of Siegen (DE)

(73) Assignee: Siemag Transplan GmbH, Netphen (DE)

(*) Notice: Under 35 U.S.C. 154(b), the term of this patent shall be extended for 0 days.

(21) Appl. No.: 09/084,855

(22) Filed: May 26, 1998

(30) Foreign Application Priority Data

May 23, 1997 (EP) .................................................. 97108365

(51) Int. Cl.[7] ................................ H04N 7/18; H04N 9/47
(52) U.S. Cl. ........................... 348/92; 348/125; 348/128; 382/141
(58) Field of Search ................................. 348/92, 90, 82, 348/86, 88, 125, 128; 382/108, 141, 149, 152

(56) References Cited

U.S. PATENT DOCUMENTS 4,319,270 * 3/1982 Kimura et al. ...................... 348/125
4,495,587 * 1/1985 Plante et al. ............................ 702/38

(List continued on next page.)

OTHER PUBLICATIONS

Bone et al, "Sensing and Control for Automated Robotic Edge Deburring", IEEE Trans. on Industrial Electronics, vol. 41, No. 2, Apr. 1994, pp. 137–146.*

Garcia et al, "Flatness Defects Detection in Rolling Products With Real–Time Vision System", IEEE Conference on Intelligent Systems Engineering, Sep. 1994, pp. 407–412.*

Primary Examiner—Vu Le
(74) Attorney, Agent, or Firm—Brown & Wood, LLP

(57) ABSTRACT

A method for the automatic detection of surface defects for continuously cast products (2) with continuous mechanical removal of the material, which products are separated into part lengths while still in the hot state and are introduced before the final rolling in a rolling train to a material removing machine (1), in particular to a grinding machine, in which the material of the continuously cast product (2) is removed as a function of the defective areas determined by a defect localising equipment (6; 7) more or less intensively from the surface(s) to be machined, which method provides that the surface defect (12a, 12b) is introduced by the defect localising equipment (6; 7) as pictorial information to a picture processing processor (11) and read in by a computer (13), comprising an integrated comparison and evaluation module (15) and connected superposed to the machine control (17), in which computer the transmitted digital pictorial information is compared in a sample recognition process with stored pictures of typical surface defects and the results like length, width and area of the defect are either directly processed and stored in a coordinate-related set of defect area (16) in accordance with a classification with regard to the relevance of the surface defects, or, after the storing in a set of surface defect data are classified in a subsequent evaluation process. The defect localising equipment is constructed as an inspection unit (6; 7) which has at least one camera (8) and a lighting equipment (9) which are arranged on a transverse girder (4) extending over the resting table (3) and the inspection unit (6; 7) is connected to a comparison and evaluation module (15) and to a computer (13) having a coordinate-related set of defect data (16).

11 Claims, 2 Drawing Sheets

U.S. PATENT DOCUMENTS

Figures 1A, 1B:
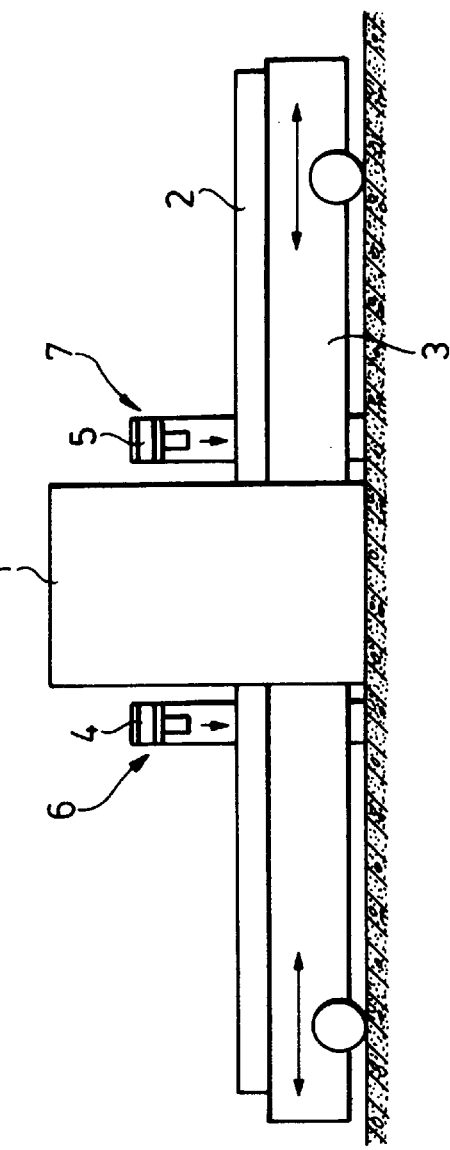

| | | | | |
|---|---|---|---|---|
| 4,519,041 | * | 5/1985 | Fant et al. | 364/552 |
| 4,539,561 | * | 9/1985 | Wulff | 340/675 |
| 4,561,104 | * | 12/1985 | Martin | 382/152 |
| 4,759,072 | * | 7/1988 | Yamane et al. | 382/152 |
| 5,379,347 | * | 1/1995 | Kato et al. | 382/141 |
| 5,517,575 | * | 5/1996 | Ladewski | 382/108 |
| 5,763,786 | * | 6/1998 | Camplin et al. | 73/643 |
| 5,845,002 | * | 12/1998 | Heck et al. | 382/110 |
| 6,064,759 | * | 5/2000 | Buckley et al. | 382/154 |

* cited by examiner

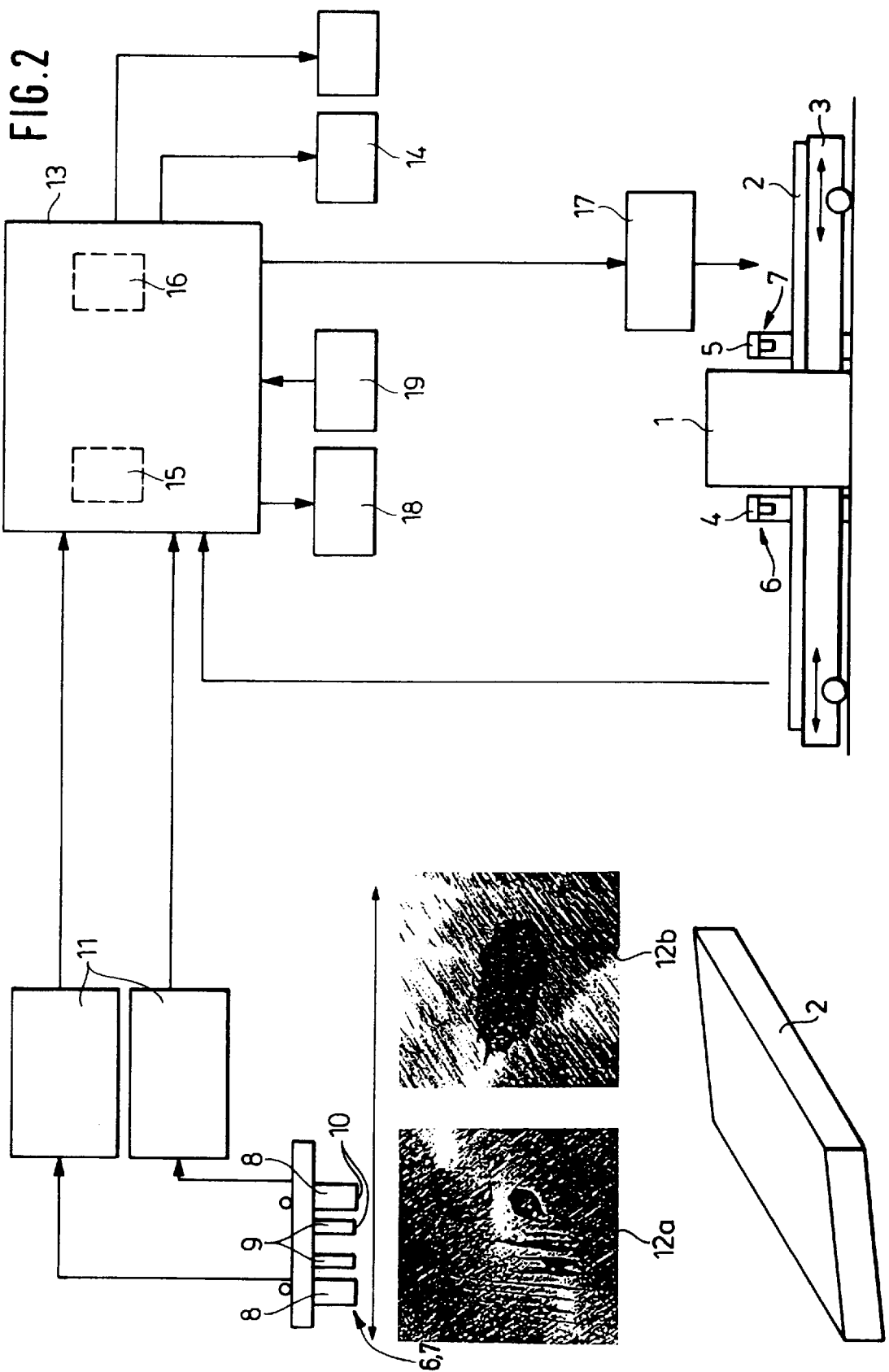

METHOD AND DEVICE FOR THE AUTOMATIC DETECTION OF SURFACE DEFECTS FOR CONTINUOUSLY CAST PRODUCTS WITH CONTINUOUS MECHANICAL REMOVAL OF THE MATERIAL

The invention concerns a method for the automatic detection of surface defects for continuously cast products with continuous mechanical removal of the material, which products are separated into part lengths while still in the hot state and are introduced before the final rolling in a rolling train to a material removing machine, in particular to a grinding machine, in which the material of the continuously cast product is removed generally or as a function of the defective areas determined by a defect localising equipment more or less intensively from the surface(s) to be machined, as well as a device to carry out the method.

Initial products, like slabs, ingots and billets made of steel and non-ferrous metal alloys, produced by the modern manufacturing method of continuous casting, represent the starting point for diverse high quality metal products, e.g. steel sheets or wires. In such continuous casting plants one or several endless cast strands are produced, which after passing through a cooling and bending section of a flame cutting or a shearing device travelling with it are divided into parts while still in the hot state. Following this the finished products, possibly after previous heating of the partial lengths, are produced in a rolling train. On this occasion surface defects inherent in the manufacturing technology, for example cracks, flat depressions and notches are also rolled in, thereby reducing the quality of the manufactured finished products to the extent that they become unfit for use. This applies particularly to high-grade sheets with high requirements with regard to the surface quality, so that such defects are not acceptable. Above all, it is therefore usual in the case of initial products made of high-grade materials to machine these prior to final rolling in special high-pressure grinding machines by grinding the surface. It is also known to remove surfaces by planing or milling.

A method of removal of the type mentioned in the introduction is known from EP-B-0 053 274. To achieve an improved surface quality which is advantageous for the further processing by removing the least possible material over the entire machining width, the removing process is carried out by pre-selected feeds in a reversing manner in the longitudinal and transverse direction of the slab and intensified as a function of the surface defects occurring. A defect localising equipment (detector or video equipment) is connected before the cutting tools, in particular grinding wheel, which continuously scans the surface for defect sources and carries out the removal process intensively corresponding to the defect signals. Accordingly, the cutting tools can be placed more or less against the surface of the slab or the part length.

Even though the use of a detector or of video equipment is known for the mechanical removal of material off continuously cast products, these defect localising equipment are used in practices, if at all, only for manual finishing work. The surfaces of continuously cast products are, as a rule, inspected visually by an operator of the grinding machine after a first general grinding cut, the defective areas are marked and are finish machined with the machine using manual control. This is carried out so that the surface machining is interrupted for the inspection of the initial product (slab, ingot, billet) and the initial product is transported with the aid of the working or resting table of the removal machine from a cabin enclosing it. For the purpose of inspection the operator has to leave the machine control stand which is not always in the vicinity of the removing machine. The search for defects and the evaluation, whether a follow-up machining is necessary thus depends on the qualification and the eyesight of the operator, so that a constant quality is difficult to ensure. The operator marks the defective areas manually, e.g. with a crayon, and approaches these for the finish machining with the aid of the video camera. Due to the surrounding conditions, e.g. heat, dust, etc. and the consequent poor visibility this is often a difficult and time-consuming task.

Finally, the maximum temperature of the initial product is limited by virtue of the unavoidable direct contact by the operator. This contradicts the effort of the operator, namely to carry out the removal at an as high as possible temperature, the reason for this being that the metals or metal alloys are easier to machine at higher temperatures and from the energy point of view it is not advisable to cool off the hot continuously case product, to inspect them and then carry out the surface machining and then be reheated for further processing. Accordingly, for slabs working temperatures between approx. 250 and 800° C. are strived for.

The object of the invention is to produce a method and a device to carry out the method, with which the previously mentioned disadvantages are eliminated and by means of which the economy and the quality of the surface machining can be improved, as well as the machining can be carried out in a process controlled automatically by a computer.

This objective is achieved by the method according to the invention by that the surface defect is introduced by the defect localising equipment as pictorial information to a picture processing processor and read in by a computer, comprising an integrated comparison and evaluation module and connected superposed to the machine control, in which computer the transmitted digital pictorial information is compared in a sample recognition process with stored pictures of typical surface defects and the results like length, width and area of the defect are either directly processed and stored in a coordinate-related set of defect data in accordance with a classification with regard to the relevance of the surface defects, or, after the storing in a set of surface defect data are classified in a subsequent evaluation process. There is also the alternative possibility to store the entire surface topology and show it on a display screen. In this manner an automated, computer-controlled logistic, continuous process management and follow-up as well as documentation of data relevant for the quality is achieved, and all this despite the rough surrounding conditions, e.g. heat, dust, vibrations, mechanical requirements, specific features of the surface of the workpiece and of the material as well as the type and expression of the surface defects. In this conjunction the invention is based on the recognition that conventional methods, known from non-destructive testing technology, which make use of thermal and magnetic principles or are based on ultrasonic, induction or laser technology, cannot be used due to the previously mentioned special conditions of surroundings and application.

In this conjunction the processing of the topology data transmitted by the processor to the computer in the comparison and evaluation module in a such a manner that the result can be filed directly in the coordinate-related set of defect data, has the advantage that further processing in the computer has to utilise only the considerably smaller coordinate-related set of defect data. An alternative according to the invention is to carry out the final classification in a following evaluation process based on the measuring errors read into the coordinate-related set of defect area.

In any case the filling of the topology data processed in the comparison and evaluation module immediately in the coordinate-related set of defect data offers the possibility of connecting the coordinate-related set of defect data on-line with the machine control stand, i.e. to transmit pictures of the defective positions immediately to the control stand.

A preferred execution of the invention provides that the coordinate-related set of defect data is transferred to the machine control by means of data transfer and the machine control converts this to automatic machining of the defect. Indeed, the machine-related degree of automation can be basically matched to suit the prevailing application-specific requirement. In this conjunction several possibilities are feasible. Thus the image of the entire surface topology can be shown on a high-resolution display screen in the operator's cabin. The operator can inspect this and decide not only as to which defects should be treated, but to drive up to the defective positions immediately. Instead of this the computer may offer only pictures of the defective positions and data regarding the dimensions and positions of the defects, whereupon the operator can choose and manually control the machining. The defective positions can be approached also automatically and the machining can be carried out either manually or automatically.

The invention also proposes to record the type and frequency of defects in a statistical module integrated in the computer, wherein the computer itself selects the defective positions and the removing tools of the removing machine are applied for an automatic machining by means of the machine control. Thus a process, fully automatic in all respect, is carried out, wherein the statistical module defines the criteria necessary for the selection of the defects to be machined.

Accordingly, the surface defects are eliminated, wherein the pictorial information of the surface is processed by a processor, read in by a computer and stored in a databank; simultaneously an on-line transmission to a display screen in the machine control stand can also take place. On this occasion it is recognised and made use of, that for the securing of the local allocation of the defects and of the initial product or workpiece the coordinates of a travel measuring system of the reciprocally moving working or resting table of the removing machine are stored in the longitudinal direction of the workpiece (X position) in the computer and the coordinates in the transverse direction of the workpiece (Y position) can be obtained by evaluating the pictorial information. The reason for this is that the defect localising equipment or the inspection unit detects both lateral edges of the workpiece and the computer is capable of processing the width allocation (Y position). Therefore, the set of data contains the complete topology of the workpiece with the pictorial information containing the X, Y coordinates.

In the case of a device for the carrying out of the method, which comprises a removing machine, in particular a grinding machine with machine tools, e.g. grinding wheels, planing tools or milling cutters, connected with a superposed computer, a resting table for the products to be machined and at least one defect localising equipment, according to the invention the defect localising equipment is constructed as an inspection unit which has at least one camera and a lighting equipment which are arranged on a transverse girder extending over the resting table. Regarding the components and devices for the optical surface inspection one can deal, in the case of the camera, with a flat or matrix or line camera and in the case of the lighting equipment with a flash unit, a spotlight or the like, which illuminate the field of inspection in an optimum manner. The number and type of the cameras depends from the desired resolution (pixels) in the defect detection (e.g. cracks with approx. 0.1 mm width occur) and the width of the workpiece. The light spectrum of the lighting equipment of the inspection unit is matched to suit these conditions and if a flash unit is used care should be taken that the flash frequency and the picture processing frequency (approx. 5 $\mu$s) are matched to suit each other. In addition, the system is designed so that all components, which are part of the processing and evaluating of the picture, have a sufficiently high machining speed and capability of data storing at a speed of approx. 1 m/s of the machining or resting table, e.g. grinding table or support of the removing tool (e.g. in the case of planing or milling).

According to a preferred development of the invention a first inspection unit is provided before and a second inspection unit after the removing machine. The fact that the inspection unit, in case of a grinding machine, cannot be positioned on the axis of the grinding wheel, i.e. in the only position which sweeps over the entire workpiece when the tool resting on the grinding table moves in the longitudinal direction under the inspection unit during the grinding operation, is compensated by this. Only by providing two inspection units, each parallel to this axis, can the inspection of the total surface be assured. In this conjunction it is recommended to superimpose the data of the individual part areas of the surface topology prepared by the two inspection units in a combination module to form a total set of data. To this end the inspection units, arranged outside the removing machine or in a cabin surrounding it, have the advantage that they are not directly influenced by the removing or grinding machining (sparking, increased dust yield, strong thermal stress, vibrations, breakage of grinding wheel, etc.). If workpieces or initial products are machined, the lengths of which is smaller than the distance between the axis of the grinding wheel and the inspection unit, a special inspection step can be integrated into the machine control. In the sense of an interruption-free and reliable operation the grinding or removing process can be supported if the initial product is relieved before the inspection by means of a mechanical cleaning process from loose contamination, e.g. grinding swarf, scales, loose flakes, etc., or, alternatively, the surface is blasted with compressed air or is vacuum cleaned.

In the case of an inspection unit having a plurality of cameras, these should be arranged in a cascading manner to enable a better recording of the measured values.

A further development provides that the camera is provided with an optical filter. These could be matched to suit the prevailing light spectrum and the influence of the disturbing light (lighting bodies, glowing sparks).

A further proposal envisages that a protective disc is positioned in front of the camera and the lighting equipment. This prevents the penetration of dust, sparks and moisture as well as damages due to mechanical contacts and represents an easily replaceable wearing part.

It is further proposed to construct the camera and the lighting equipment thermally encased and/or cooled. The purpose of this is the protection from the considerable heat radiation of the continuously cast product, which can be very hot. For cooling gaseous (air, nitrogen) or liquid (water) media may be used, depending on the local conditions, and the protection of the data and energy transmission lines by insulation may also be recommended.

Further features and advantages of the invention become apparent from the patent claims and the following description, in which the subject matter of the invention is explained in detail on the embodiment of a grinding machine. They show in:

FIG. 1—a traversing grinding table of a grinding machine with an associated inspection unit, shown diagrammatically in front view (pat FIG. a) and total view (part FIG. b), and FIG. 2—the grinding unit according to FIG. 1b with an attached computer for the automatic detection of surface defects, shown diagrammatically as a block circuit.

A slab grinding machine, not shown in detail and adequately known per se (cf., for example, the previously mentioned EP-B-0 053 274) has at least one grinding wheel, which is enclosed on the outside in a grinding cabin 1. The workpiece to be machined, in this case a slab 2, is resting on a grinding table 3 which can move back and forth in the longitudinal direction. On each side of the grinding cabin 1 a girder 4 and 5 is situated, extending transversely over the grinding table 3 with the slab 2, on which girders a first and a second, respectively, inspection unit 6 and 7 are provided which can traverse transversely with the aid of a linear drive (cf. FIG. 1b). In this embodiment the inspection units 6, 7 consist of two cameras 8 and lighting equipment 9 (cf. FIG. 2) associated with them, wherein both the cameras 8 and the lighting equipment 9 are thermally encased and/or cooled as well as provided with a protective disc 10 in front of them.

As a modification for the above described grinding machine with a table a portal grinding machine may also be used, in which case the workpiece rests on stationary devices and the grinding portal travels over the workpiece in a reversing manner.

For the automated, computer-controlled logistical carrying out and following up of the process as well as the documentation of the data relevant for the quality, according to FIG. 2 processors 11 are allocated to the inspection units 6, 7, which process the surface defects detected by the cameras 8 on the surface of the slab 2, in the form of pictorial informations 12a, 12b. This data, reproducing the topography of the surface of the slab 2, is read in by a superordinated computer 13 and stored in a databank 14. The computer 13 has as integrated components a comparison and evaluation module 15 and a coordinate-related set of defect data 16; in addition, it is connected to the machine control 17 of the grinding machine.

The digital pictorial information are compared in the comparison and evaluating module 15 in a sample recognition process with stored pictures of typical surface defects (cf. the reference numbers 12a and 12b in FIG. 2) and the results are stored in the coordinate-related set of defect data 16. The classification with regard to relevance, e.g. size of the defective area, length or width of the defect, is carried out in a subsequent evaluating process. Alternatively, the topology data, transmitted to the computer can be processed immediately by the comparison and evaluation module 15 and the results fed into a coordinate-referenced set of surface data. The on-line computer 13, connected to a high resolution display screen 18 in the operator's cabin, makes it feasible to convey to the operator the image of the overall surface topology, so that the operator can carry out an inspection and can engage by means of a keyboard 19 the grinding wheel for a following machining of the defect. An alternative, whereby only pictures of the defective areas are presented and the defective areas area approached manually or automatically and the machining is carried out manually or automatically, i.e. to carry out a fully automatic inspection and machining process, is also feasible.

What is claimed is:

1. A method of eliminating surface defects in continuously cast products, comprising the steps of:

providing, in a rolling train upstream of final rolling means, a material removing machine for machining surface defects on a surface of the cast products;

providing a computer connected with a control unit of the material removing machine as a higher order unit and including an inter-grated comparison and evaluation unit in which pictures of typical surface defects are stored;

delivering a part length of a continuous cast product to the material removing machine;

determining surface defects by defect localizing means that introduces the surface defects as pictorial information to a picture processing processor; communicating information, which is processed by the picture processing processor, to the computer in which the pictorial information is compared in a sample recognition process with the stored picture of typical surface defects, and the results including length, width and an area of the defect are one of directly processed and stored in a coordinate-related set of defect date in accordance with a classification with regard to relevance of surface defects and, after storing, a set data are classified in a subsequent evaluation process; and communicating the defect data from the computer to the control unit of the material removing machine which controls operation of a material removing machine tool that is brought only against the defect areas of a treated surface.

2. The method according to claim 1, wherein the defect data communicating step comprises the step of data transfer to the control unit of the coordinate-related set of defect data, with the control unit converting the defect data for automatic machining of the defect surface.

3. The method according to claim 2, wherein the coordinate-related set of data is transmitted to the control unit on-line.

4. The method according to claim 1, comprising the steps of recording type and frequency of the surface defects in a statistical module integrated in the computer, and selecting, by the computer, defective positions of the material removing tools and the removing tools themselves.

5. A device for eliminating surface defects in continuously cast products, comprising a material removing machine having a material removing tool and a control unit connected with a higher order computer; a resting table for receiving a part length of a continuously cast products; defect localizing means formed as an inspection unit which has at least one camera and a lighting equipment which are arranged on a transverse girder extending over the resting table, with the inspection unit being connected to a comparison and evaluation module having a coordinate-related set of defect data.

6. The device according to claim 5, wherein the inspection unit comprises a first inspection unit is located in front of the material removing machine and a second inspection unit located after the removing machine.

7. The device according to claim 5, wherein a plurality of cameras are provided in a cascading manner.

8. The device according to claim 5, wherein the camera is provided with an optical filter.

9. The device according to claim 5, wherein the inspection unit is displaceable on the transverse girder.

10. The device according to claim 5, wherein protective disc is positioned in front of the camera and the lighting equipment (9).

11. The device according to claim 5, wherein the camera and the lighting equipment area at least one of thermally encased and cooled.

* * * * *